(12) United States Patent
Balisky

(10) Patent No.: US 9,702,793 B2
(45) Date of Patent: Jul. 11, 2017

(54) VARIABLE VOLUME SAMPLE CAPTURE DEVICE

(71) Applicant: Todd A Balisky, Corona, CA (US)

(72) Inventor: Todd A Balisky, Corona, CA (US)

(*) Notice: Subject to any disclaimer, the term of this patent is extended or adjusted under 35 U.S.C. 154(b) by 171 days.

(21) Appl. No.: 14/659,113

(22) Filed: Mar. 16, 2015

(65) Prior Publication Data

US 2016/0274002 A1    Sep. 22, 2016

(51) Int. Cl.
*G01N 1/14* (2006.01)

(52) U.S. Cl.
CPC ....... *G01N 1/14* (2013.01); *G01N 2001/1427* (2013.01)

(58) Field of Classification Search
CPC .......................... G01N 1/14; G01N 2001/1427
USPC ....................................... 73/863.73
See application file for complete search history.

(56) References Cited

U.S. PATENT DOCUMENTS

| | | |
|---|---|---|
| 813,977 A | 2/1906 | Koenig |
| 2,697,842 A | 12/1954 | Meyer |
| 2,834,654 A | 5/1958 | Murayama |
| 3,120,789 A | 2/1964 | Anthon |
| 3,186,800 A | 6/1965 | Stickler |
| 3,881,360 A | 5/1975 | Jurado |
| 4,356,727 A | 11/1982 | Brown et al. |
| 4,361,253 A | 11/1982 | Flynn et al. |
| 4,700,561 A | 10/1987 | Dougherty |
| 4,873,057 A | 10/1989 | Roberson et al. |
| 4,895,808 A | 1/1990 | Romer |
| 5,454,268 A | 10/1995 | Kim |
| 5,637,092 A | 6/1997 | Shaw |
| 5,662,166 A | 9/1997 | Shammai et al. |
| 5,736,654 A | 4/1998 | Dubois |
| 6,099,502 A * | 8/2000 | Duchon ................ A61B 6/504 128/DIG. 12 |
| 6,235,002 B1 | 5/2001 | Carver, Jr. et al. |
| 6,257,076 B1 | 7/2001 | Snyder et al. |
| 6,293,429 B2 | 9/2001 | Sadler |
| 6,301,980 B1 | 10/2001 | Munderloh |

(Continued)

FOREIGN PATENT DOCUMENTS

| | | |
|---|---|---|
| CA | 2438137 | 8/2002 |
| CN | 103698469 | 4/2014 |

(Continued)

*Primary Examiner* — Hezron E Williams
*Assistant Examiner* — Marrit Eyassu
(74) *Attorney, Agent, or Firm* — Kirk A. Buhler; Buhler & Associates

(57) ABSTRACT

Improvements in a variable volume capture device are disclosed to capture a variable amount of sample. The variable amount is controlled by a linear actuator that produces a variable and adjustable stroke length that capture the programmed amount of fluid in the syringe barrel. Air or other supernatant fluid can be separated and expelled at this point. The captured fluid is then dispensed out of the syringe barrel for further testing and analysis. The capture device is then able to drain or flush the sample. Valves located on each side of the syringe barrel allow for sample collecting, dispensing and draining to ensure that the capture device is free to collect new samples. The variable volume capture device can have changeable syringe and barrel diameters and lengths to accommodate larger or smaller ranges of samples.

19 Claims, 3 Drawing Sheets

(56) References Cited

U.S. PATENT DOCUMENTS

Figure 1:
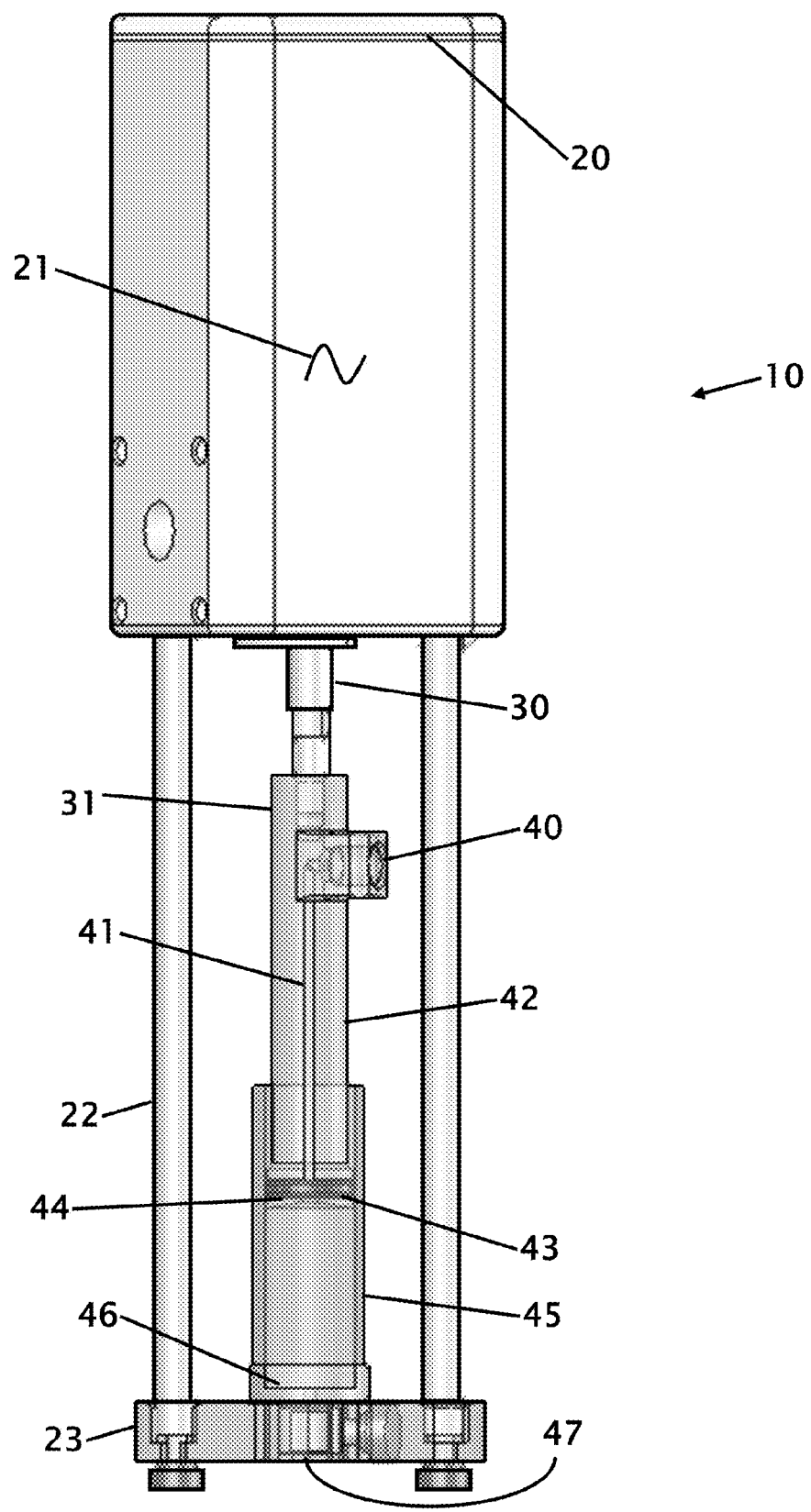

| | | |
|---|---|---|
| 6,319,466 B1 | 11/2001 | Markovsky |
| 6,571,562 B2 | 6/2003 | Wilcox |
| 6,835,191 B2 | 12/2004 | Lee et al. |
| 6,988,547 B2 | 1/2006 | Goodwin et al. |
| 7,111,757 B1 * | 9/2006 | O'Brien ................ B01L 3/0206 222/1 |
| 7,246,664 B2 | 7/2007 | Shammai et al. |
| 7,438,857 B2 | 10/2008 | Masaro |
| 7,753,238 B2 | 7/2010 | Kirschenbuhler et al. |
| 7,767,146 B2 | 8/2010 | Kirschenbuhler |
| 7,824,373 B2 * | 11/2010 | Kim .................... A61M 5/2053 604/140 |
| 8,476,063 B2 | 7/2013 | Jovanovich et al. |
| 8,512,278 B2 * | 8/2013 | Tennican ............. A61J 1/2096 604/228 |
| 2001/0036645 A1 | 11/2001 | McNeirney et al. |
| 2003/0132243 A1 * | 7/2003 | Engel ................... H05K 13/046 222/61 |
| 2005/0015056 A1 | 1/2005 | Duchon et al. |
| 2005/0056416 A1 | 3/2005 | Holt et al. |
| 2005/0197538 A1 | 9/2005 | Leaton et al. |
| 2008/0060413 A1 | 3/2008 | Miyamoto |
| 2009/0019953 A1 | 1/2009 | Bommarito et al. |
| 2009/0143699 A1 | 6/2009 | Wu et al. |
| 2011/0151479 A1 | 6/2011 | Stevens et al. |
| 2012/0046557 A1 | 2/2012 | Kiani |
| 2012/0103076 A1 | 5/2012 | Schwarz et al. |
| 2013/0110401 A1 | 5/2013 | Hsu et al. |
| 2013/0184677 A1 * | 7/2013 | Py ..................... A61M 5/31593 604/506 |
| 2013/0203171 A1 | 8/2013 | Sportsman |
| 2013/0239705 A1 * | 9/2013 | Namikawa ............... G01N 1/14 73/863.23 |
| 2014/0087413 A1 | 3/2014 | Newbold et al. |
| 2014/0114238 A1 | 4/2014 | Lee et al. |
| 2014/0219311 A1 | 8/2014 | Plotnikov et al. |
| 2014/0274522 A1 | 9/2014 | Davis et al. |
| 2014/0295532 A1 | 10/2014 | Ray |

FOREIGN PATENT DOCUMENTS

| | | |
|---|---|---|
| CN | 203519573 | 4/2014 |
| EP | 0399497 | 11/1990 |
| EP | 1723978 | 11/2006 |
| EP | 1897575 | 3/2008 |
| EP | 2756167 | 7/2014 |
| WO | WO2004009238 | 1/2004 |

* cited by examiner

VARIABLE VOLUME SAMPLE CAPTURE DEVICE

CROSS REFERENCE TO RELATED APPLICATION

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

Field of the Invention

This invention relates to improvements in a variable volume capture device. More particularly, the present variable volume capture device that allows for capture and delivery of a representative and exact volume of liquid for online (or at-line) chemical analysis. In particular, this is intended for use on the sampling and analysis of multiple sample sources.

Description of Related Art Including Information Disclosed Under 37 CFR 1.97 and 1.98

Many industries today use chemical processing in, for example, mining, food processing, refining, water treatment, recycling, and semiconductor manufacture, metal and plastic surface treatment, and so on. In most cases, monitoring of the process chemistry by chemical analysis is necessary to maintain the product quality and consistency. For analysis in general and for online (or at-line) chemical analysis in particular, it is usually necessary to obtain a liquid sample and to dispense it accurately. For this it is important that the sample be representative of the whole and that the amount captured and dispensed be controlled. To obtain a representative sample, particularly when different sample sources and compositions are anticipated, it is necessary to remove completely and desirable to purge out efficiently old sample. And for reasons of both obtaining a representative sample and of dispensing a consistent and accurate volume of sample, it is necessary to remove air bubbles from the sample and sample chambers. In addition, a process with multiple analyses and corresponding multiple analytical procedures can benefit from a device or system that captures and delivers variable, selectable, but still accurate, sample volumes.

Historically, mechanized syringes and burettes have worked well for some of these analytical functions. That is, they can be operated to draw (fill) any amount within their range, and likewise precisely dispense a specific amount. The Kloehn (Las Vegas, Nev.) model V6 syringe and syringe drive, for example, perform these functions and can include a valve at the syringe tip to select fluid source and destination(s) as well. But as the syringe chamber is effectively a fluidic dead-end, this is not a flow-through device and consequently sample change-over is either inefficient or incomplete. Although one could orient the unit so that the syringe tip points downward to facilitate drainage, this would defeat the air-purging that is achieved in the normal, upward direction.

A number of patents and or publications have been made to address these issues. Exemplary examples of patents and or publication that try to address this/these problem(s) are identified and discussed below.

U.S. Pat. No. 6,235,002 issued May 22, 2001 to Edward Lawrence Carver, Jr et al. discloses a Syringe for Use in Fluid-Handling Apparatus. The syringe has a housing, a substantially fixed seal, a solid or closed-tip plunger, an internal passageway formed between the housing and the plunger, and at least two ports on the housing with at least one port located at each end of the passageway for the passage of fluids and the elimination of gas. While the syringe takes a sample, there can be a cross contamination and the sample is fixed in volume.

U.S. Patent publication Number 20080060413 was published on Mar. 13, 2008 to Masao Miyamoto et al., discloses a Flow Analysis System. The deaerator comprises a liquid-containing means variable in internal volume for containing the liquid together with gas bubbles included in the liquid. While the dearator can extract a sample, the dearator only extracts a sample from a flow and not from a standing pool.

U.S. Patent Publication Number 20140219311 was published by Valerian Plotnikov et al., discloses an Isothermal Titration Microcalorimeter Apparatus and Method of Use. This patent describes an automatic pipette assembly for an isothermal titration micro calorimetry system. The pipette system is basically a single use sampling system because when a sample is taken the syringe holder can be contaminated.

What is needed is a variable volume capture device that allows for a capturing and delivery of a representative and exact volume of liquid for chemical analysis.

BRIEF SUMMARY OF THE INVENTION

It is an object of the variable volume capture device to capture a variable amount of sample. The variable amount is controlled by a linear actuator that produces a variable and adjustable stroke length that capture the programmed amount of fluid into the syringe barrel. The captured fluid is then dispensed out of the syringe barrel for further testing and analysis of the captured fluid.

It is another object of the variable volume capture device to flush itself from a previous sample of fluid. If the syringe barrel is not flushed, cross contamination of test fluids can cause false readings of the captured samples. Valves located on each side of the syringe barrel allow for sample collecting, dispensing and draining to ensure that the capture device is free to collect new samples.

It is still another object of the variable volume capture device to allow for changing syringe and barrel diameters and lengths to accommodate larger or smaller ranges of samples. While the linear drive shaft can capture a variable amount of fluid with each sample, capture of small samples that have a volume of the plunger fluid path can be imprecise, whereby changing to a smaller syringe and barrel will provide greater efficiency. At the other extreme, if a large sample that exceeds the volume of a syringe barrel, a larger syringe and barrel can be utilized.

Various objects, features, aspects, and advantages of the present invention will become more apparent from the following detailed description of preferred embodiments of

BRIEF DESCRIPTION OF THE SEVERAL VIEWS OF THE DRAWING(S)

Figure 2:
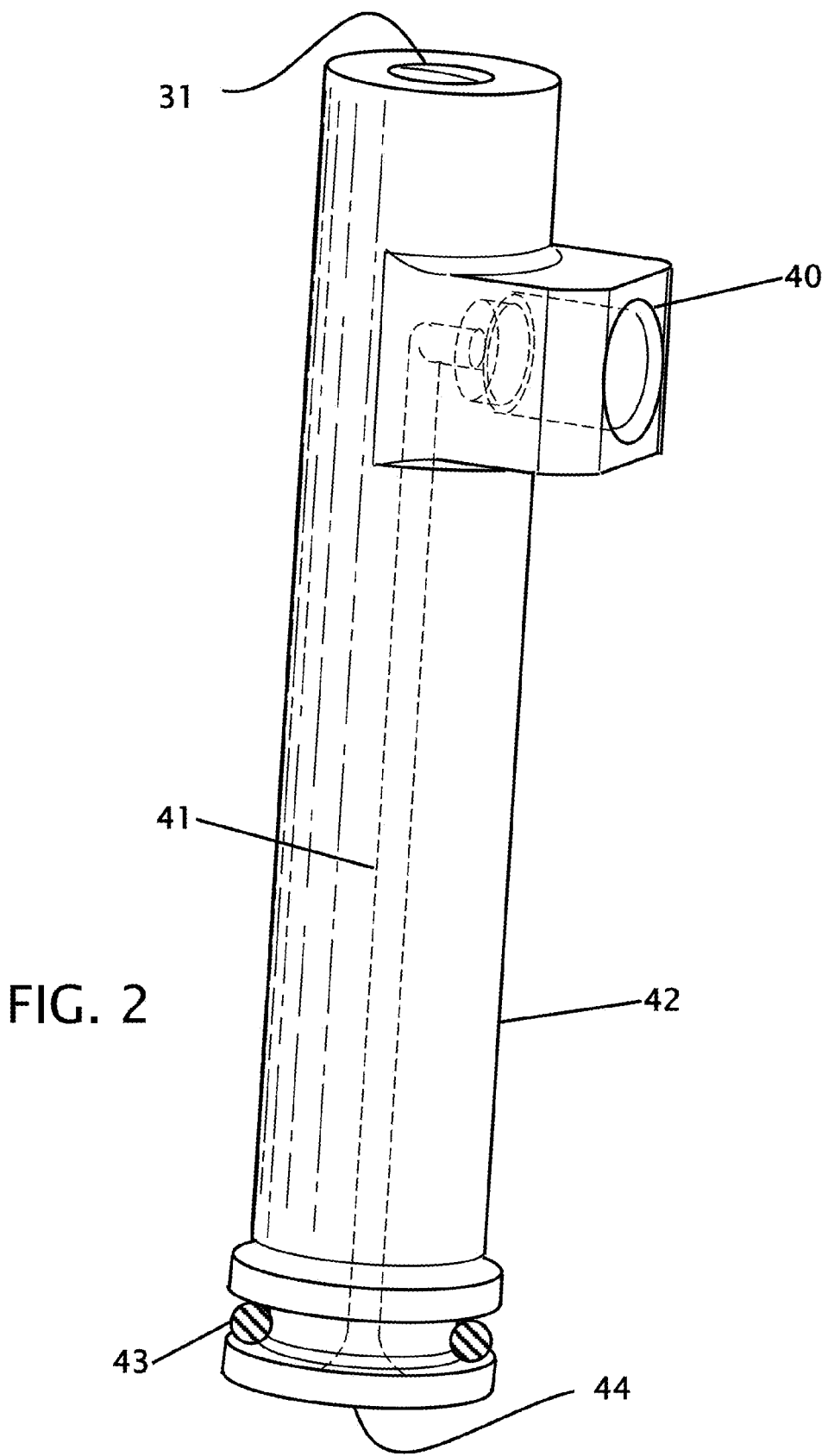
Figure 5:
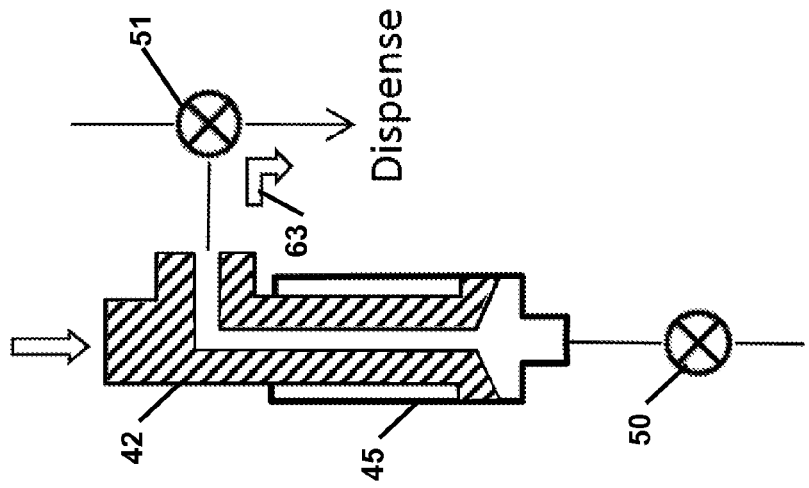
Figure 4:
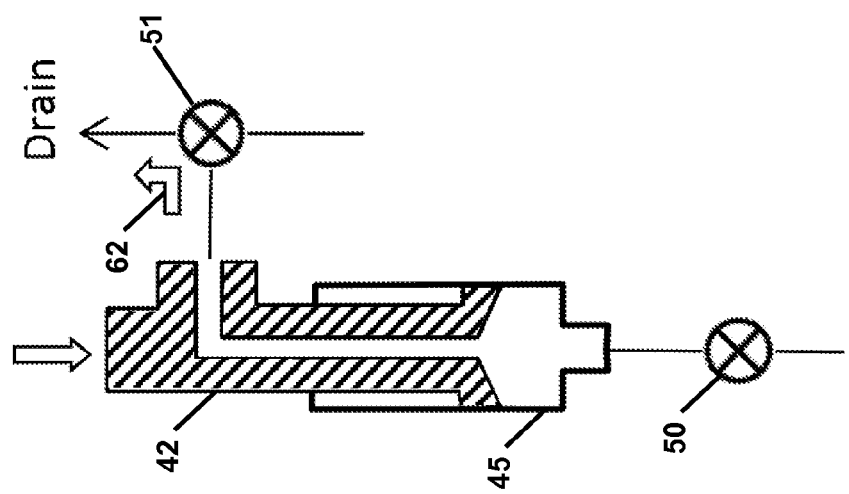
Figure 3:
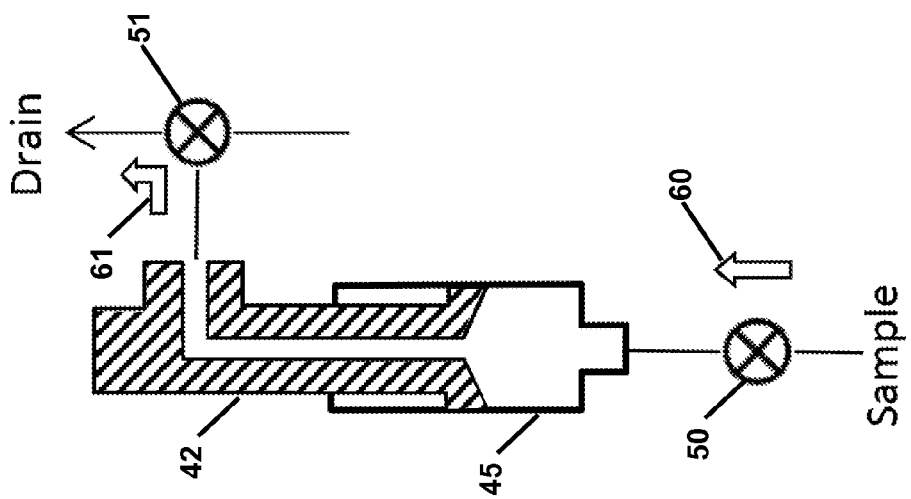

FIG. 1 shows the syringe and plunger assembly.
FIG. 2 shows a detailed view of the plunger.
FIG. 3 shows the plunger in a sample capture mode.
FIG. 4 shows the plunger in an air expel mode.
FIG. 5 shows the plunger in a sample dispense mode.

DETAILED DESCRIPTION OF THE INVENTION

FIG. 1 shows the syringe and plunger assembly. This figure shows the motor housing 21 having a motor access plate 20 on top of top of the motor housing 21. The motor housing has a linear drive shaft 30 that moves the sample collecting device in a linear motion into the sample that is being collected. The structure has a syringe bracket frame 22 that connects to a syringe bracket base 23. The linear actuator can be pneumatic, hydraulic or electrically powered.

There is a threaded coupling 31 that connects the linear drive shaft 30 to the plunger 42. The plunger 42 has an upper fluid port 40 where captured fluid is expelled to a drain or dispensed for testing. Within the plunger 42 is a fluid path 41 for captured fluid to travel. The bottom of the plunger 42 is retained in the syringe barrel 45 and is sealed with a plunger seal 43 at the funnel entrance 44. The bottom of the syringe barrel 45 has a syringe nose piece 46 connecting the syringe cavity to the lower fluid port 47.

FIG. 2 shows a detailed view of the plunger 42. The top of the plunger 42 has a threaded coupling 31 for connection to the linear drive shaft 30 (shown in FIG. 1). In this figure, the plunger 42 shows the open upper fluid port 40. The upper fluid port 40 is shown connected to the fluid path 41 down to the funnel entrance 44. The bottom of the plunger 42 shows the plunger seal 43.

Modes of Operation

FIG. 3 shows the plunger 42 in a sample capture mode. The first mode of operation is sample capture. For this, the plunger 42 is positioned so as to increase the internal volume in the reservoir. This volume can be chosen to accommodate the necessary volume for analysis plus any amount that is to be discarded for the purpose of priming downstream fluidics and expelling air bubbles. Sample is then allowed to flow through the reservoir, if pressurized, or pumped through, if not, until the reservoir and exit path are filled.

In this embodiment, the reservoir is a syringe barrel 45, but in general can be a cylindrical chamber with rigid walls, an opening at the top end for a plunger 42, and a smaller opening at the lower end as a fluid orifice. On the plunger 42 there is a sliding fluid seal 43 between the plunger 42 and the reservoir, such as can be made with Teflon, polyethylene, or an elastomer. In our embodiment, an elastomer O-ring was preferred as it could be readily replaced upon wear. At the lower orifice is a valve 50 used to stop or allow sample flow 60. It is opened, for example, during sample capture and closed during sample dispense. In some cases, when back flushing is not required, a check valve can be used for valve 50 to simplify the hardware. The fluid path 41 passes through the plunger 42 and optionally through path 61 to additional valve(s) 51 that select fluid destination.

An alternate first mode (prior to sample capture) is sample flush, that is, flushing with sample. This is desirable when there is a sample change over and it is necessary to remove the residual of the previous fluid. In this case the plunger 42 is positioned so as to minimize the internal reservoir volume and so minimize the flush time and volume required. This change over can be further accelerated by introducing air into the sample, which acts to break up laminar flow and push fluids out of pockets.

FIG. 4 shows the plunger 42 in an air expel mode. The next mode after sample capture is air expel. Air that is entrained in the sample such as in the form of small bubbles will rise in the reservoir to the underside of the plunger 42 after stopping the flow. In this embodiment, flow 62 is stopped by closing the sample inlet valve 50 at the funnel entrance 44. Once air has separated to the top of the reservoir, a partial reduction in reservoir volume, in this case by driving the plunger downward, expels the air out 62 through the plunger 42 from where it is discarded to a drain or sent to the test vessel. If it may be discarded to the test vessel then valve 51 is not required. An inverted funnel shape in the plunger 42 underside with the exit path 40 at its apex facilitates bubble collection and removal. The plunger can be fabricated of transparent or translucent material to facilitate visual inspection and confirmation of this air removal. At this point, an additional amount of fluid is typically dispensed into the test vessel to prime the fluid path from the plunger 42 outlet to there. (The test vessel is rinsed prior to dispensing and testing the final sample aliquot.) In another contemplated embodiment, a sample is drawn through the assembly by a pump located after the syringe, between valve 51 and the drain. In this way, a single pump can be used for sampling multiple sources.

FIG. 5 shows the plunger 42 in a sample dispense mode. The next mode is sample dispense. During this, with the sample inlet valve 50 closed and any dispense valves routed to the test vessel, the plunger 42 is moved downward to reduce the reservoir 45 volume and dispense sample to the vessel. The distance of plunger 42 movement is used to select and control the volume of sample delivered. Since the prior sample and compressible air are removed from the system, sample volume accuracy is maximized. The linear actuator and valves are controlled by a computer where the sample size and the operation of the components can operate automatically to quickly sample, air expel and dispense 63 the captured fluid. While the sample is described as fluid, it is contemplated that the sample can be multiple phases of media comprising, for example, polar and non-polar liquids such as water and oil that will be separated or dispensed in the same manner.

The typical last mode is cleanup. In this mode the reservoir 45 is emptied and/or rinsed by cycling the plunger 42 and flushing with water and/or air. Flushing in the reverse direction is especially effective and can be facilitated by a funnel shape 44 at the bottom of the reservoir.

Thus, specific embodiments of a variable volume capture device have been disclosed. It should be apparent, however, to those skilled in the art that many more modifications besides those described are possible without departing from the inventive concepts herein. The inventive subject matter, therefore, is not to be restricted except in the spirit of the appended claims.

SEQUENCE LISTING

Not Applicable.

The invention claimed is:

1. A variable volume capture device comprising:
a linear actuator secured to a plunger at a first end of said plunger;
said linear actuator is programmable for stroke length;
said plunger having a second end with a funnel entrance;
said plunger having an upper fluid port between said first end and said second end;
said funnel entrance being connected to said fluid port;
said second end of said plunger fitting within a syringe barrel at a first end of said syringe barrel;
said syringe barrel having a second end with a syringe nose piece and a lower fluid ports;
a first valve connected to said lower fluid port;
whereby said linear actuator moves said plunger within said syringe barrel to withdraw a sample through said lower fluid port and into said syringe barrel and further, said linear actuator moves said plunger to expel said sample out said upper fluid port;
said syringe barrel is cleaned by cycling said plunger; and
wherein said syringe barrel is mounted to a base, and said linear actuator is located distal from said base, and a plurality of frame members support said linear actuator above said plunger and said syringe barrel on said base.

2. The variable volume capture device according to claim 1 wherein said stroke length is adjustable.

3. The variable volume capture device according to claim 2 wherein said adjustable stroke length varies the volume of said sample.

4. The variable volume capture device according to claim 1 wherein said first valve opens to capture or draw a sample into said syringe barrel.

5. The variable volume capture device according to claim 4 that further includes a second valve wherein said second valve opens to drain.

6. The variable volume capture device according to claim 5 wherein said first valve closes and said linear actuator moves said plunger into said syringe barrel to expel air.

7. The variable volume capture device according to claim 6 wherein said linear actuator moves said plunger into said syringe barrel to expel said sample directly for further analysis.

8. The variable volume capture device according to claim 7 wherein said syringe barrel cleaning includes a flushing mode whereby air or pressurized gas and a rinsing solvent are introduced into said syringe barrel in either direction.

9. The variable volume capture device according to claim 1 wherein said variable volume capture device has a top mounted motor driven linear actuator.

10. The variable volume capture device according to claim 1 wherein said plunger and said syringe barrel are replaced with at least a second plunger and at least a second syringe barrel to alter a volume range of said sample.

11. The variable volume capture device according to claim 1 wherein said plunger and said syringe body are located between said linear actuator and said base.

12. The variable volume capture device according to claim 1 wherein said syringe nose piece is secured to said base.

13. The variable volume capture device according to claim 1 that further includes a seal between said plunger and said syringe barrel.

14. The variable volume capture device according to claim 13 wherein said seal is selected from a group consisting of Teflon, polyethylene, or elastomer.

15. The variable volume capture device according to claim 1 wherein said linear actuator is pneumatic, hydraulic or electrically powered.

16. The variable volume capture device according to claim 1 wherein linear actuator and said first valve are controlled by a computer.

17. The variable volume capture device according to claim 1 wherein said funnel entrance is funnel shaped.

18. The variable volume capture device according to claim 1 wherein said plunger is transparent or translucent to facilitate visual inspection and confirmation of air removal or phase separation.

19. The variable volume capture device according to claim 1 further includes drawing an additional amount of fluid and dispensing said additional fluid to a test vessel to prime a fluid path from said plunger.

* * * * *